US 6,770,463 B2

(12) United States Patent
Chiarello et al.

(10) Patent No.: US 6,770,463 B2
(45) Date of Patent: Aug. 3, 2004

(54) PROCESS FOR THE PREPARATION OF CHIRAL ISOFLUOROENES

(75) Inventors: John Francis Chiarello, Newtown, PA (US); Brian Lee Buckwalter, Yardley, PA (US); Timothy Claude Barden, Holland, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 121 days.

(21) Appl. No.: 09/921,188

(22) Filed: Aug. 2, 2001

(65) Prior Publication Data

US 2002/0032351 A1 Mar. 14, 2002

Related U.S. Application Data

(60) Provisional application No. 60/222,733, filed on Aug. 3, 2000, now abandoned.

(51) Int. Cl.$^7$ .......................... C12P 17/16; C07C 43/02
(52) U.S. Cl. ...................... 435/118; 435/197; 435/122; 435/128; 435/132; 435/155; 568/639; 568/634; 568/630; 568/631; 568/647; 558/411; 558/423; 546/346; 548/578
(58) Field of Search ................................. 435/197, 118, 435/122, 128, 132, 155; 568/639, 634, 630, 631, 647; 558/411, 423; 546/346; 548/578

(56) References Cited

U.S. PATENT DOCUMENTS

| 3,880,991 A | 4/1975 | Dickel et al. ............... 260/247 |
| 4,137,324 A | * 1/1979 | Elliott et al. ................. 424/282 |
| 5,998,673 A | 12/1999 | Barnes et al. ............... 568/634 |

FOREIGN PATENT DOCUMENTS

| FR | 2004826 | 12/1969 |
| GB | 1 580 193 | 11/1980 |
| WO | WO 88/08416 | 11/1999 |

* cited by examiner

Primary Examiner—Francisco Prats
(74) Attorney, Agent, or Firm—Keil & Weinkauf

(57) ABSTRACT

There is provided a process for the preparation of a chiral insecticidal and acaricidal compound of formula I.

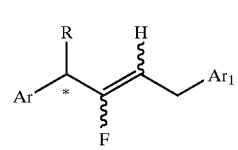

Also provided are intermediate compounds useful in the process of the present invention.

11 Claims, No Drawings

PROCESS FOR THE PREPARATION OF CHIRAL ISOFLUOROENES

This application claims priority from provisional application(s) serial No. 60/222,733 filed on Aug. 3, 2000 now abandoned.

BACKGROUND OF THE INVENTION 1,4-diaryl-2-fluoro-2-butenes and a method for their preparation are described in U.S. Pat. No. 5,998,673. Said compounds are useful as insecticidal and acaricidal agents and for protecting plants from damage caused by insect and acarid attack and infestation. Although U.S. Pat. No. 5,998,673 discloses and claims optical isomers of said 1,4-diaryl-2-fluoro-2-butenes, it does not provide a method for their preparation.

It is therefore an object of the present invention to provide a process for the preparation of chiral 1,4-diaryl-2-fluoro-2-butenes.

It is also an object of the present invention to provide intermediates useful in said process.

These and other objects of the present invention will become more apparent from the detailed description thereof set forth below.

SUMMARY OF THE INVENTION

There is provided a process for the preparation of a chiral compound of formula I

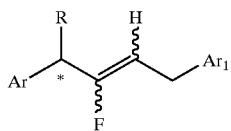

wherein
Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is $C_1$–$C_4$alkyl, $C_1$–$C_4$haloalkyl, $C_3$–$C_6$cycloalkyl or $C_3$–$C_6$halocycloalkyl;
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
the (E)- and (Z)-isomers thereof, which process comprises the following steps:

a) treating a racemic ester of formula II

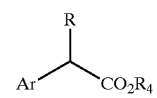

wherein Ar and R are defined as hereinabove and $R_4$ is $C_1$–$C_4$alkyl with an esterase to form a first mixture of either R-acid IIIa and S-ester IIIb

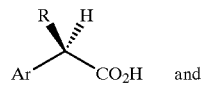

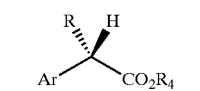

or of S-acid IIIc and R-ester IIId

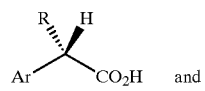

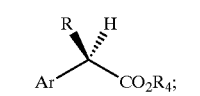

b) separating said acid IIIa or IIIc from said ester IIIb or IIId;

c) reducing said acid IIIa or IIIc or said ester IIIb or IIId to obtain a chiral alcohol IV having the R- or S-configuration

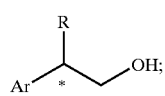

b) reacting said chiral alcohol with an arylsulfonyl halide $Ar_2SO_2X$
wherein $Ar_2$ is phenyl, p-chlorophenyl, or p-tolyl, and X is chloro, bromo or fluoro to afford a sulfonate of formula V

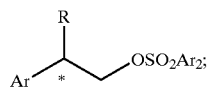
V e) reacting said sulfonate V with a cyanide-delivering agent to afford a nitrile of formula VI

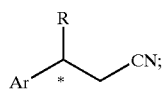
VI f) hydrolysing said nitrile VI to afford an acid of formula VII

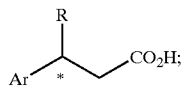
VII g) esterifying said acid VII with an alcohol $R_1OH$, wherein $R_1$ is $C_1-C_4$ alkyl to afford an ester of formula VIII

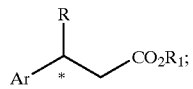
VIII h) fluorinating said ester to afford a fluoro-ester of formula IX

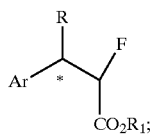
IX i) reacting said fluoro ester with an aldehyde $Ar_1CH_2CHO$, wherein $Ar_1$ is defined as hereinabove, in a solvent in the presence of a base to afford a second mixture of 4 chiral diastereomeric hydroxy-esters of formula X

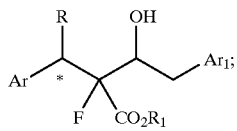
X j) optionally separating said second mixture X into a third mixture Xa and a fourth mixture Xb, each mixture having two chiral diastereomers;
k) treating said hydroxy-ester mixture X, Xa or Xb with an acylating agent $R_2COX_1$, wherein $R_2$ is $C_1-C_4$alkyl and $X_1$ is Cl, Br or $R_2COO$, to afford a fifth mixture of 4 chiral diastereomeric acyloxy esters XI, a sixth mixture of 2 acyloxy esters of formula XIa, or a seventh mixture of 2 chiral diastereomeric acyloxy esters XIb

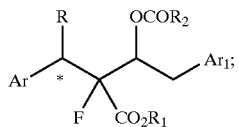
XI l) optionally separating said sixth or seventh mixture into essentially pure chiral diastereomeric acyloxy esters;
m) hydrolyzing said pure chiral acyloxy esters or mixtures of esters of formula XI to afford a hydroxy-acid of formula XII

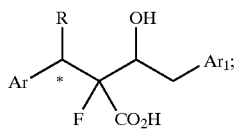
XII and
n) heating said hydroxy-acid XII with an arylsulfonyl halide $Ar_3SO_2X_2$, wherein $Ar_3$ is phenyl, p-chlorophenyl, or p-tolyl, and
$X_2$ is chloro or bromo to afford the desired chiral compound of formula I.

The invention further provides chiral intermediate compounds useful in the process of this invention.

DETAILED DESCRIPTION OF THE INVENTION

Although chiral 1,4-diaryl-2-fluoro-2-butenes are described in U.S. Pat. No. 5,998,673, no method for their preparation is disclosed.

Advantageously, the present invention provides a method for the preparation of chiral compounds of formula I

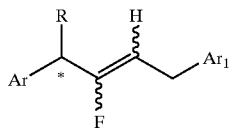
I wherein Ar, R and $Ar_1$ are defined as above.

In accordance with the process of this invention racemic ester II is enzymatically hydrolyzed with an esterase to afford a first mixture of acid IIIa having the R-configuration, and unhydrolyzed ester IIIb, having the S-configuration, which is separated. Said acid IIIa or said ester IIIb is reduced to obtain a chiral alcohol IV having the R- or S-configuration; said alcohol is reacted with an arylsulfonyl halide $Ar_2SO_2X$ to afford a sulfonate of formula V; said sulfonate is treated with a cyanide-delivering agent to afford a nitrile of formula VI; said nitrile is hydrolyzed to yield an acid of formula VII; said acid is esterified with an alcohol $R_1OH$ to yield an ester of formula VIII; said ester is fluorinated to afford a fluoro-ester of formula IX; said fluoro-ester is reacted with an aldehyde $Ar_1CH_2CHO$ in a solvent in the presence of a base to afford a second mixture of 4 chiral diasteromeric hydroxy-esters of formula X; optionally said second mixture can be separated into a third mixture Xa and a fourth mixture Xb, each mixture having two chiral diastereomers; said hydroxy-ester mixture X, Xa, or Xb is treated with an acylating agent $R_2COX$, to afford a fifth mixture of 4 chiral diasteromeric acyloxy esters XI, a sixth mixture of 2 acyloxy esters of formula XIa, or seventh mixture of chiral diasteromeric acyloxy esters XIb; optionally, said sixth or seventh mixture can be separated into to essentially pure chiral diastereomeric acyloxy esters; said pure chiral acyloxy esters or mixtures of esters of formula XI are hydrolyzed to a hydroxy acid of formula XII; and finally, said hydroxy acids are heated with an arylsulfonyl halide $Ar_3SO_2X_2$ to afford the desired chiral compound of formula I. The process is depicted in Flow Diagram I wherein $R_4$ is depicted as methyl.

The wavy lines in structural formula I represent either the E isomeric or the Z isomeric configuration about the carbon-carbon double bond.

Flow Diagram I

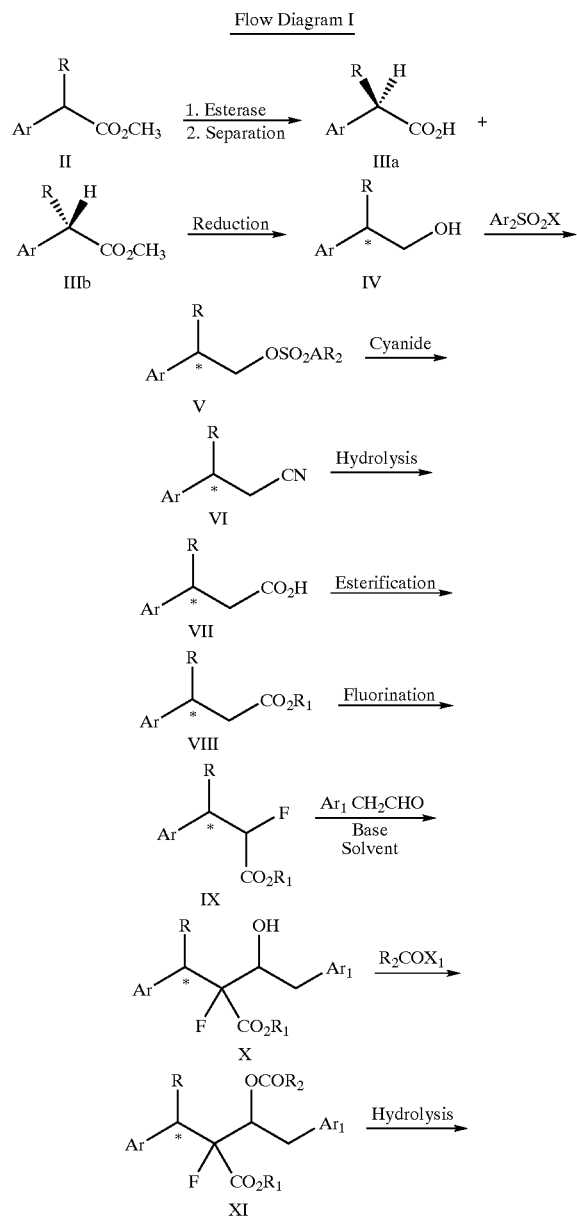

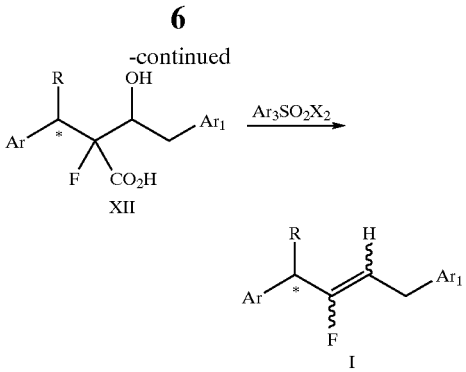

Non-polar solvents suitable for use in the process of the invention are essentially water-free solvents such as aromatic hydrocarbons (e.g. toluene, benzene, xylene, naphthalene or the like, preferably toluene), halogenated aromatic hydrocarbones (e.g. chlorobenzene, dichlorobenzene or the like), hydrocarbons (e.g. chloroform, methylene chloride, dichlorethane, or the like, or any of the conventional, preferably water imiscible, organic non-polar solvents.

Preferred non-polar solvents suitable for use in the process of the invention are hydrocarbons and aromatic hydrocarbons such as hexane, heptane, toluene, ethylbenzene or the like.

Polar aprotic solvents suitable for use in the inventive process are dimethylformamide, dimethyl-sulfoxide, tetrahydrofuran, diethyl ether, or the like.

Preferred polar aprotic solvents suitable for use in the process of the invention are dimethylformamide and dimethylsulfoxide.

Derivitizing agents suitable for use in the formation of V are triarylphosphine/trialkylphosphines such as triphenylphosphine and triethylphosphine and carbon tetrahalides such as carbon tetrachloride and carbon tetrabromide as well as arylsulfonyl halides such as p-toluene sulfonyl chloride, p-toluene sulfonyl bromide, p-toluene sulfonyl fluoride, benzenesulfonyl bromide, benzenesulfonyl chloride, benzenesulfonyl fluoride, p-chlorobenzenesulfonyl bromide, p-chlorobenzenesulfonyl chloride and p-chlorobenzenesulfonylfluoride or alkylsulfonyl halides such as methane sulfonyl chloride, preferably p-toluene sulfonyl chloride. Suitable bases are resin-bound tertiary organic bases such as polystyrene diisopropyl ethylamine and tertiary organic bases such as triethyl amine and diisopropyl ethyl amine and pyridine, preferably triethlamine. Reaction temperatures may vary from about 0° C. to reflux, preferably from about 25° C. to about 50° C., more preferably about 25° C.

Cyanide delivering agents suitable for the formation of nitrile VI are metal cyanides, alkali earth metal cyanide and alkali metal cyanide such as potassium cyanide, zinc cyanide and sodium cyanide, preferably sodium cyanide. Reaction temperatures may vary from about 25° C. to about 180° C., preferably from about 50° C. to about 125° C., more preferably about 90° C.

Suitable agents for the hydrolysis of nitrile VI are aqueous acids such as sulfuric acid or hydrochloric acid in the presence of or without the presence of alcohol such as methanol, ethanol, propanol, isopropanol, n-butanol, isobutanol and t-butyl alcohol, aqueous alkali or alkali earth bases such as potassium hydroxide, calcium hydroxide and sodium hydroxide, preferably sodium hydroxide. Reaction temperatures may vary from about 25° C. to about 100° C., preferably from about 50° C. to about 100° C., more preferably about 100° C.

Reaction temperatures suitable for the esterifiecation of acid VII vary from about −10° C. to about 40° C., preferably about −10° C. to about 10° C., more preferably about 0° C.

Bases suitable for the generation of the anion of if ester VIII are alkali metal hexaalkylsilylamides such as lithium hexamethylsilylamide or sodium hexamethylsilylamide, alkali metal dialkyl amides such as sodium diisopropylamide, metal hydrides such as sodium hydride and potassium hydride, preferably lithium diisopropyl amide.

Reaction temperatures vary from about −78° C. to about 25° C., preferred starting temperature is about −78° C., with the ending temperature about 25° C.

Suitable bases for treating fluoroester IX are metal hydrides such as sodium hydride and potassium hydride, alkali metal hexa-alkylsilylamide such as sodium hexamethylsilylamide or lithium hexamethysilylamide, alkali metal dialkylamides such as sodium diisopropylamide or lithium diisopropylamide, preferably lithium diisopropylamide.

Suitable bases for the formation of I are pyridine and substituted pyridines, preferably collidine. Reaction temperatures vary from about 25° C. to about 200° C., preferably from about 100° C. to about 200° C., more preferably from about 170° C. to about 180° C.

In actual practice, racemic ester II in water is treated with an esterase enzyme, preferably horse liver esterase, preferably between pH 7.1–8.0 to yield a first mixture of either R-acid IIIa and S-ester IIIb or S-acid IIIc and R-ester IIId; said acid can be separated from said ester by standard extraction techniques, preferably with aqueous sodium bicarbonate followed by acidification with mineral acid, preferably dilute hydrochloric acid and reextraction, or more preferably by chromatographic techniques, preferably on silica gel; said acid IIIa or IIIc is reduced with diborane, or said ester IIIb or IIId is reduced with diisobutylaluminum hydride to afford chiral alcohol IV having the R- or the S-configuration; said alcohol IV is reacted with at least one molar equivalent of a sulfonyl halide $Ar_2SO_2Cl$, preferably an arylsulfonyl chloride in a non-polar aprotic solvent, preferably methylene chloride, in the presence of at least one molar equivalent of a base, preferably a tertiary organic base, more preferably triethylamine to afford sulfonate V; said sulfonate V is reacted with a cyanide-delivering agent, preferably an alkali metal cyanide, more preferably sodium cyanide, in a polar aprotic solvent, preferably dimethylsulfoxide, to yield nitrile VI; nitrile VI is hydrolized in the presence of aqueous acid or base, preferably dilute aqueous sodium hydroxide followed by acidification of the resulting salt with strong mineral acid, preferably concentrated hydrochloric acid, to yield acid VII. Acid VII is esterified with an alcohol $R_1OH$, preferably present in excess, in the presence of a strong acid catalyst, preferably anhydrous hydrogen chloride gas, to yield ester VIII.

Said ester is fluorinated, preferably by generating its anion with a base, preferably an alkali metal amide, more preferably lithium diisopropyl amide in an aprotic solvent, preferably tetrahydrofuran, followed by quenching said anion with an electrophilic fluorinating agent, preferably an N-fluoroimide, more preferably N-fluorobenzenesulfonimide to yield fluoro ester IX; said fluoro ester IX is reacted with an aldehyde $Ar_1CH_2CHO$ in the presence of a base, preferably an alkali metal amide, more preferably lithium diisopropylamide, in an aprotic solvent, preferably tetrahydrofuran, to afford a second mixture of 4 chiral diasteromeric hydroxy-esters of formula X; advantageously said second mixture X may be optionally separated, preferably by chromatographic techniques, more preferably on silica gel, into a third mixture Xa and a fourth mixture Xb, each mixture having two chiral diastereomers; said hydroxy-ester mixture X, Xa or Xb is treated with an acylating agent $R_2COX_1$, preferably an acid anhydride $(R_2CO)_2O$, more preferably acetic anhydride, in a non-polar solvent, preferably methylene chloride in the presence of an acylation catalyst, preferably N,N-dimethylaminopyridine, to afford a fifth mixture of 4 chiral diastereomeric acyloxy esters XI, a sixth mixture of 2 aryloxy esters of formula XIa, or a seventh mixture of 2 chiral diasteromeric acyloxy esters of formula XIb; advantageously said sixth or seventh mixture are optionally separated preferably by chromatographic techniques, more preferably with silica gel into essentially pure chiral diastereomeric acyloxy esters; said pure chiral acyloxy esters or mixtures of esters of formula XI are hydrolyzed with acid or base, preferably dilute aqueous metal hydroxide, more preferably dilute aqueous sodium hydroxide followed by acidification with a strong mineral acid, preferably concentrated hydrochloric acid, to afford a hydroxy-acid of formula XII; said hydroxy-acid is treated in the presence of an aryl-sulfonyl halide $Ar_3SO_2X_2$, preferably an arylsulfonyl chloride, more preferably p-toluene sulfonyl chloride, to afford the desired chiral compound of formula 1.

The present invention also provides chiral compounds of formula XIII

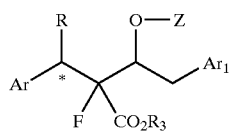

XIII wherein
Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is $C_1$–$C_4$alkyl, $C_1$–$C_4$haloalkyl, $C_3$–$C_6$cycloalkyl or $C_3$–$C_6$halocycloalkyl;
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and $R_3$ is H or $C_1$–$C_4$alkyl; and Z is H or $COR_2$, wherein $R_2$ is $C_1$–$C_4$alkyl.

Preferred compounds of the present invention are those wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and R is $C_1$–$C_4$alkyl or $C_3$–$C_6$cycloalkyl.

More preferred compounds are those wherein $Ar_1$ is phenyl optionally substituted with one to three halogen groups; and R is $C_3$–$C_6$cycloalkyl.

Most preferred compounds are those selected from the group consisting of methyl (2S,3S)-2-[(R)-(4-chlorophenyl)(cyclopropyl)methyl]-2-fluoro-4-(4-fluoro-3-phenoxyphenyl)butanoate;

methyl (2R,3R)-2-[(R)-(4-chlorophenyl)(cyclopropyl)methyl]-2-fluoro-4-(4-fluoro-3-phenoxyphenyl)butanoate;

methyl (2S,3R)-2-[(R)-(4-chlorophenyl)(cyclopropyl)methyl]-2-fluoro-4-(4-fluoro-3-phenoxyphenyl)butanoate;

methyl (2R,3S)-2-[(R)-(4-chlorophenyl)(cyclopropyl)methyl]-2-fluoro-4-(4-fluoro-3-phenoxyphenyl)butanoate;

methyl (2S,3S)-2-[(S)-(4-chlorophenyl)(cyclopropyl)methyl]-2-fluoro-4-(4-fluoro-3-phenoxyphenyl)butanoate;

methyl (2R,3R)-2-[(S)-(4-chlorophenyl)(cyclopropyl)methyl]-2-fluoro-4-(4-fluoro-3-phenoxyphenyl)butanoate;

methyl (2S,3R)-2-[(S)-(4-chlorophenyl)(cyclopropyl)methyl]-2-fluoro-4-(4-fluoro-3-phenoxyphenyl)butanoate;

methyl (2R,3S)-2-[(S)-(4-chlorophenyl)(cyclopropyl)methyl]-2-fluoro-4-(4-fluoro-3-phenoxyphenyl)butanoate;

methyl (2S,3S)-3-(acetyloxy)-2-[(S)-(4-chlorophenyl)(cyclopropyl)methyl]-2-fluoro-4-(4-fluoro-3-phenoxyphenyl)butanoate;

methyl (2R,3R)-3-(acetyloxy)-2-[(S)-(4-chlorophenyl)(cyclopropyl)methyl]-2-fluoro-4-(4-fluoro-3-phenoxyphenyl)butanoate;

methyl (2R,3R)-3-(acetyloxy)-2-[(S)-(4-chlorophenyl)(cyclopropyl)methyl]-2-fluoro-4-(4-fluoro-3-phenoxyphenyl)butanoate;

methyl (2S,3R)-3-(acetyloxy)-2-[(S)-(4-chlorophenyl)(cyclopropyl)methyl]-2-fluoro-4-(4-fluoro-3-phenoxyphenyl)butanoate;

methyl (2S,3S)-3-(acetyloxy)-2-[(R)-(4-chlorophenyl)(cyclopropyl)methyl]-2-fluoro-4-(4-fluoro-3-phenoxyphenyl)butanoate;

methyl (2R,3R)-3-(acetyloxy)-2-[(R)-(4-chlorophenyl)(cyclopropyl)methyl]-2-fluoro-4-(4-fluoro-3-phenoxyphenyl)butanoate;

methyl (2R,3S)-3-(acetyloxy)-2-[(R)-(4-chlorophenyl)(cyclopropyl)methyl]-2-fluoro-4-(4-fluoro-3-phenoxyphenyl)butanoate;

methyl (2S,3R)-3-(acetyloxy)-2-[(R)-(4-chlorophenyl)(cyclopropyl)methyl]-2-fluoro-4-(4-fluoro-3-phenoxyphenyl)butanoate;

(2S,3S)-2-[(S)-(4-chlorophenyl)(cyclopropyl)methyl]-2-fluoro-4-(4-fluoro-3-phenoxyphenyl)-3-hydroxybutanoic acid;

(2R,3R)-2-[(S)-(4-chlorophenyl)(cyclopropyl)methyl]-2-fluoro-4-(4-fluoro-3-phenoxyphenyl)-3-hydroxybutanoic acid;

(2R,3S)-2-[(S)-(4-chlorophenyl)(cyclopropyl)methyl]-2-fluoro-4-(4-fluoro-3-phenoxyphenyl)-3-hydroxybutanoic acid;

(2S,3R)-2-[(S)-(4-chlorophenyl)(cyclopropyl)methyl]-2-fluoro-4-(4-fluoro-3-phenoxyphenyl)-3-hydroxybutanoic acid;

(2S,3S)-2-[(R)-(4-chlorophenyl)(cyclopropyl)methyl]-2-fluoro-4-(4-fluoro-3-phenoxyphenyl)-3-hydroxybutanoic acid;

(2R,3R)-2-[(R)-(4-chlorophenyl)(cyclopropyl)methyl]-2-fluoro-4-(4-fluoro-3-phenoxyphenyl)-3-hydroxybutanoic acid;

(2R,3S)-2-[(R)-(4-chlorophenyl)(cyclopropyl)methyl]-2-fluoro-4-(4-fluoro-3-phenoxyphenyl)-3-hydroxybutanoic acid, and (2S,3R)-2-[(R)-(4-chlorophenyl)(cyclopropyl)methyl]-2-fluoro-4-(4-fluoro-3-phenoxyphenyl)-3-hydroxybutanoic acid.

The present invention additionally provides chiral compounds of formula XIV

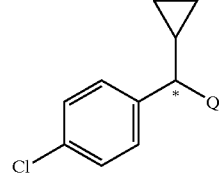

(XIV)

wherein

Q is —$CO_2H$; —$CO_2CH_3$; —$CH_2OH$; —$CH_2OSO_2Ar_2$; —$CH_2CN$; —$CH_2CO_2H$; —$CH_2CO_2R_1$; or —$CHFCO_2R_1$;

$Ar_2$ is phenyl, p-chlorophenyl, or p-tolyl; and $R_1$ is $C_1$–$C_4$alkyl.

Most preferred compounds are selected from the group consisting of (2R)-2-(4-chlorophenyl)-2-cyclopropylethyl 4-methylbenzenesulfonate;

(2S)-2-(4-chlorophenyl)-2-cyclopropylethyl 4-methylbenzenesulfonate;

(3R)-3-(4-chlorophenyl)-3-cyclopropylpropanenitrile;

(3S)-3-(4-chlorophenyl)-3-cyclopropylpropanenitrile;
(3R)-3-(4-chlorophenyl)-3-cyclopropylpropanoic acid;
(3S)-3-(4-chlorophenyl)-3-cyclopropylpropanoic acid;
methyl (3R)-3-(4-chlorophenyl)-3-cyclopropylpropanoate;
methyl (3S)-3-(4-chlorophenyl)-3-cyclopropylpropanoate;
methyl (3R)-3-(4-chlorophenyl)-3-cyclopropyl-2-fluoropropanoate;
methyl (3S)-3-(4-chlorophenyl)-3-cyclopropyl-2-fluoropropanoate;

In order to present a clear understanding of the invention, the following examples are set forth below. These examples are merely illustrative, and are not to be understood as limiting the scope and underlying principles of the invention in any way.

EXAMPLE 1

Preparation of (2R)-(4-chlorophenyl)(cyclopropyl) ethanoic acid and Methyl (2S)-(4-chlorophenyl)(cyclopropyl)ethanoate

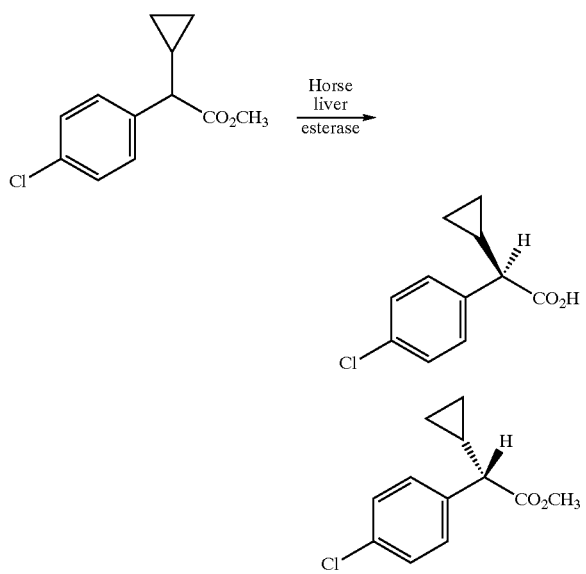

Horse liver esterase (4.6 g horse liver acetone powder, Sigma Chemical Co.) is suspended in water (200 ml) at room temperature and the pH is adjusted to 7.5 with 1.0 M sodium hydroxide. Methyl (2RS)-(4-chlorophenyl)(cyclopropyl)ethanoate (7.0 g, 31.4 mol) is added and stirring is continued at room temperature with the addition of 1.0 M sodium hydroxide as needed to maintain the pH at 7.1–8.0. After 14 ml of base had been consumed, the pH was brought to 3 with 10% hydrochloric acid, ethyl acetate is added and the mixture is filtered through diatomaceous earth. The organic phase is washed with brine, dried over anhydrous sodium sulfate, filtered and concentrated in vacuo. Flash chromatography affords (2R)-(4-chlorophenyl)(cyclopropyl)ethanoic acid (2.5 g, 37.9%) and recovered ester (4.1 g). The ester was resubjected to the hydrolysis conditions with additional horse liver esterase (1.0 g) for an extended period during which an additional 4.4 ml of 1.0 M sodium hydroxide is consumed. Acidification, workup and purification as described above affords methyl (2S)-(4-chlorophenyl)(cyclopropyl)ethanoate (3.1 g, 36.2%) The enantiomeric excess of (2R)-(4-chlorophenyl)(cyclopropyl) ethanoic acid (as the methyl ester) and (2R)-(4-chlorophenyl)(cyclopropyl)ethanoic acid are determined with the chiral NMR shift reagent Eu(hfc)$_3$ to be >96:4 and >98:2 respectively.

EXAMPLE 2

Preparation of (2R)-2-(4-chlorophenyl)-2-cyclopropylethanol

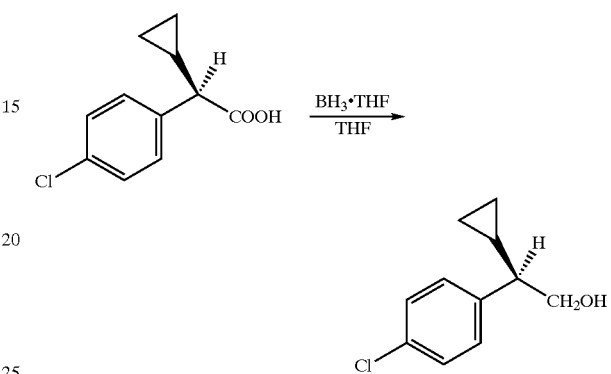

To a stirred solution of (2R)-(4-chlorophenyl)(cyclopropyl)ethanoic acid (7.25 g, 34.4 mmol) in tetrahydrofuran (200 ml) at 0° C. under nitrogen is added dropwise over one hour borane-tetrahydrofuran complex (58 ml of a 1.0 solution in tetrahydrofuran, 58 mmol). The solution is warmed to room temperature and stirred for an additional 4 h. The reaction mixture is cooled to 0° C. and carefully quenched by the dropwise addition of water: THF(1:1, 50 ml). The mixture is diluted with ethyl acetate (250 ml) and washed with water (250 ml). The organic layer is dried over anhydrous sodium sulfate and concentrated in vacuo. The residue is purified by column chromatography on silica gel eluting with ether:hexane (25:75 to 40:60) to afford the title compound as a colorless syrup (5.70 g, 84%) which is characterized by $^1$HNMR, $^{13}$CNMR and mass spectral analyses.

EXAMPLE 3

Preparation of (2S)-2-(4-chlorophenyl)-2-cyclopropylethanol

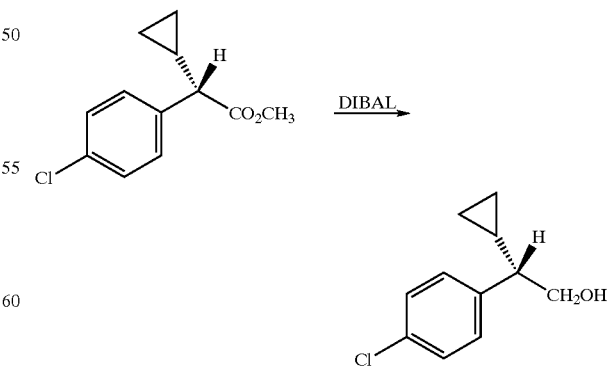

To a stirred solution of methyl (2S)-(4-chlorophenyl)(cyclopropyl)ethanoate (7.72 g, 34.4 mmol) in methylene chloride (300 ml) at −78° C. under nitrogen is added diisobutyl aluminum hydride (86 ml of a 1.0 M solution in methylene chloride, 86.0 mmol). The reaction mixture is allowed to warm to room temperature and stirred for an additional hour. The reaction is quenched by the addition of saturated aqueous ammonium chloride and then filtered. The organic layer is separated, dried over anhydrous sodium sulfate and concentrated in vacuo. The residue is chromatographed on silica gel eluting with ether:hexane (15:85) to afford the title compound as a colorless liquid (5.45 g, 80%) which is characterized by $^1$HNMR, $^{13}$CNMR and mass spectral analyses.

EXAMPLE 4

Preparation of (2R)-2-(4-Chlorophenyl)-2-cyclopropylethyl 4-methylbenzenesulfonate

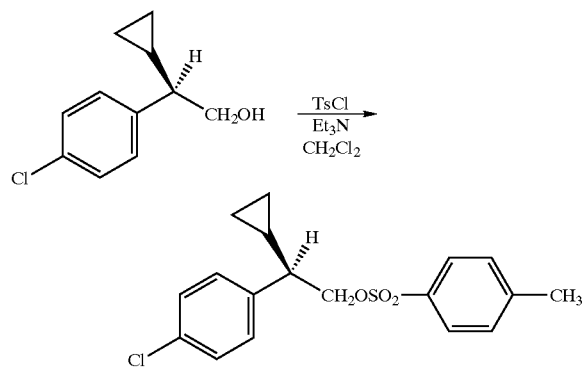

(2R)-2-(4-Chlorophenyl)-2-cyclopropylethanol (6.50 g, 33.0 mmol), tosyl chloride (7.86 g, 41.0 mmol) and 6.0 ml of triethylamine (6.0 ml) are dissolved in dichloromethane (150 ml) and allowed to stir for 3 days. The reaction mixture is washed successively with 1 N HCl (100 ml), water (100 ml) and saturated brine solution (100 ml). The organic layer is dried over anhydrous sodium sulfate and concentrated in vacuo. The residue is chromatographed on silica gel eluting with ether:hexane (10:90 to 25:75) to afford the title compound as a colorless oil (11.1 g, 96%) which is characterized by $^1$HNMR, $^{13}$CNMR and mass spectral analysis.

EXAMPLE 5

Preparation of (2S)-2-(4-Chlorophenyl)-2-cyclopropylethyl 4-methylbenzenesulfonate

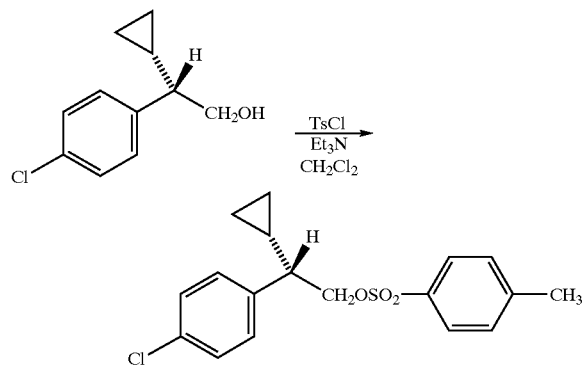

Using the procedure of Example 4, (2S)-2-(4-chlorophenyl)-2-cyclopropylethanol yields the title compound as a colorless liquid which is characterized by $^1$HNMR, IR and mass spectral analysis.

EXAMPLE 6

Preparation of (3R)-3-(4-chlorophenyl)-3-cyclopropylpropanenitrile

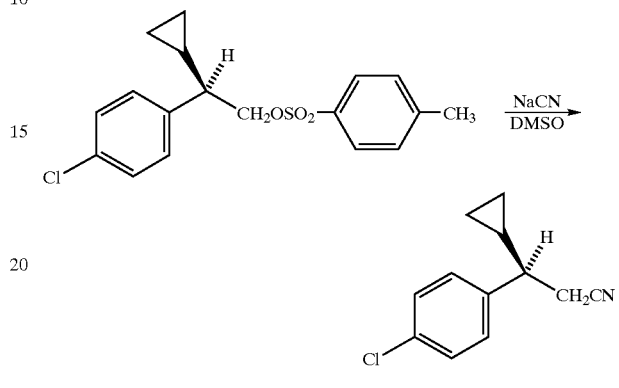

A mixture of (2R)-2-(4-chlorophenyl)-2-cyclopropylethyl 4-methylbenzenesulfonate (11.00 g, 31.3 mmol) and NaCN (4.62 g, 94.3 mmol) in dimethyl sulfoxide (100 ml) is heated at to 90° C. for 3 hours. The dimethyl sulfoxide was removed in vacuo and the resulting mixture is partitioned between water (200 ml) and diethyl ether (200 ml). The organic layer is dried over anhydrous sodium sulfate and concentrated in vacuo. The residue chromatographed on silica gel eluting with ether:hexane (25:75) to afford the title compound as a colorless oil (5.62 g, 87%) which is characterized by $^1$HNMR, IR and mass spectral analyses.

EXAMPLE 7

Preparation of (3S)-3-(4-chlorophenyl)-3-cyclopropylpropanenitrile

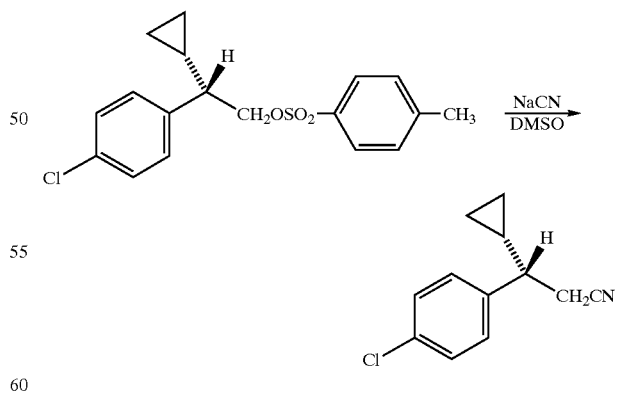

Using the procedure of Example 6, (2S)-2-(4-chlorophenyl)-2-cyclopropylethyl 4-methylbenzenesulfonate yields the title compound as a colorless liquid which is characterized by $^1$HNMR, IR and mass spectral analyses.

EXAMPLE 8

Preparation of (3R)-3-(4-Chlorophenyl)-3-cyclopropylpropanoic acid

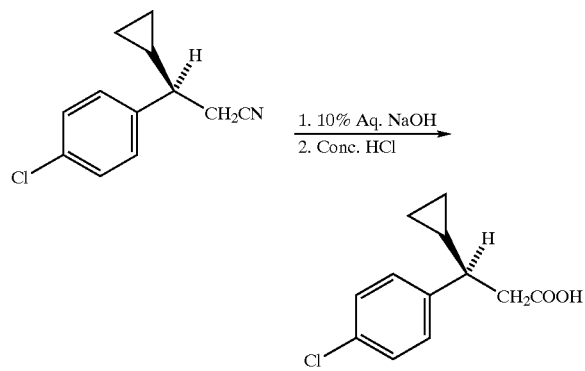

(3R)-3-(4-Chlorophenyl)-3-cyclopropylpropanenitrile (5.30 g, 25.8 mmol) is refluxed for 18 hours in a mixture of methanol (100 ml) and a 10% aqueous sodium hydroxide (100 ml). Methanol is removed in vacuo, the residual solution is cooled to 0° C. and acidified to pH 4 with concentrated hydrochloric acid. The aqueous layer is extracted with ethyl acetate (100 ml). The organic layer is dried over anhydrous sodium sulfate and concentrated in vacuo to afford the title compound as a colorless liquid (5.79 g, 100%) which is characterized by $^1$HNMR, IR and mass spectral analysis and used without further purification.

EXAMPLE 9

Preparation of (3S)-3-(4-chlorophenyl)-3-cyclopropylpropanoic acid

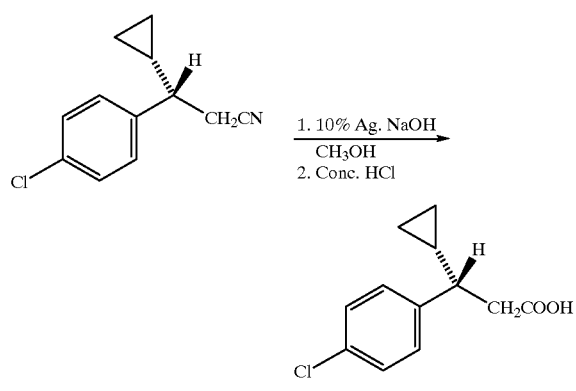

Using the procedure of Example 8, (3S)-3-(4-chlorophenyl)-3-cyclopropylpropanenitrile yields the title compound as a colorless oil, which is characterized by $^1$HNMR, IR and mass spectral analyses.

EXAMPLE 10

Preparation of Methyl (3R)-3-(4-chlorophenyl)-3-cyclopropylpropanoate

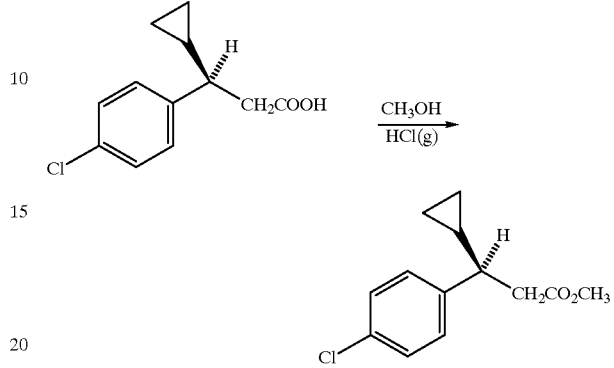

Hydrogen chloride gas is bubbled into a solution of (3R)-3-(4-chlorophenyl)-3-cyclopropylpropanoic acid (5.79 g, 25.85 mmol) in methanol (100 ml) at 0° C. for 30 seconds. The solution is allowed to warm to room temperature and stirred for 18 hours. The solution is concentrated in vacuo, diluted with chloroform (100 ml) and washed with 5% aqueous sodium bicarbonate (100 ml). The organic layer is dried over anhydrous sodium sulfate and concentrated in vacuo. The residue is chromatographed on silica gel eluting with ether:hexane (10:90) to yield the title compound as a colorless liquid (5.15 g, 84% from (3R)-3-(4-chlorophenyl)-3-cyclopropylpropanenitrile) which is characterized by $^1$HNMR, IR and mass spectral analyses.

EXAMPLE 11

Preparation of Methyl (3S)-3-(4-chlorophenyl)-3-cyclopropylpropanoate

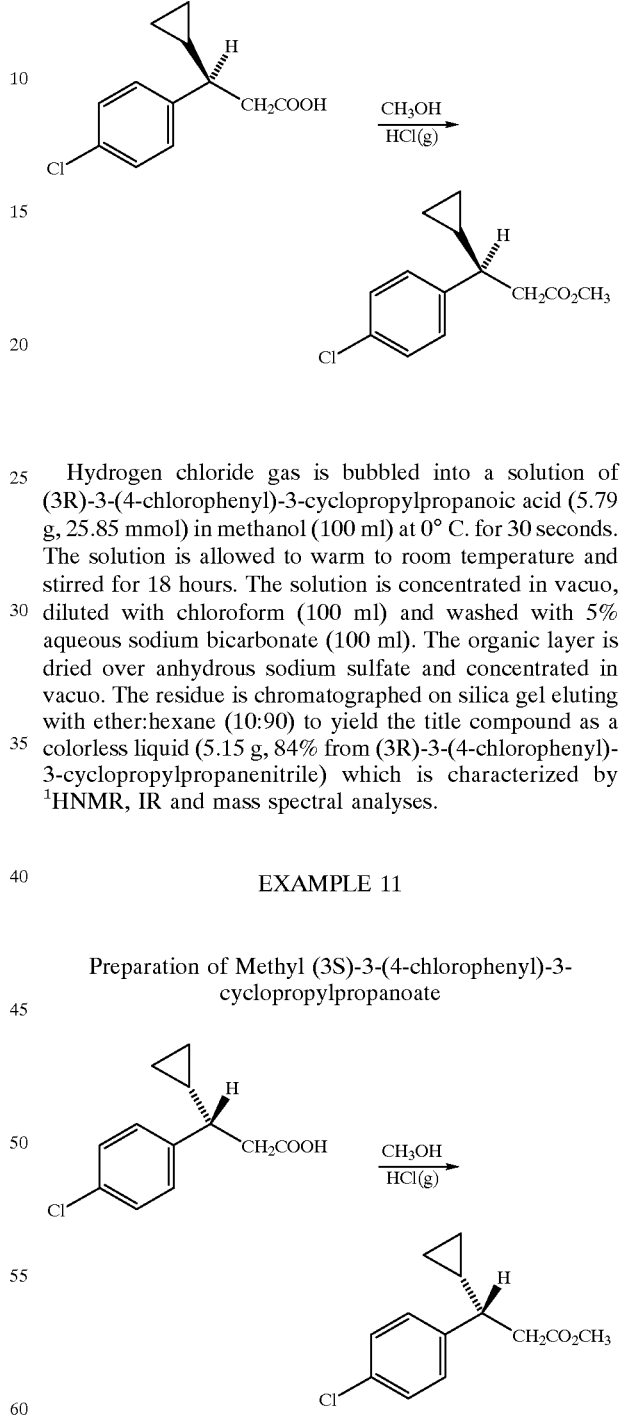

Using the procedure of Example 10, (3S)-3-(4-chlorophenyl)-3-cyclopropylpropanoic acid yields the title compound as a colorless liquid which is characterized by $^1$HNMR, IR and mass spectral analyses.

EXAMPLE 12

Preparation of Methyl (3R)-3-(4-chlorophenyl)-3-cyclopropyl-2-fluoropropanoate

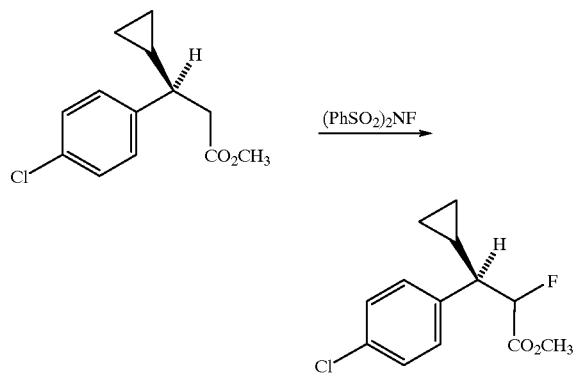

To a stirred solution of lithium diisopropyl amide (30 mmol) in dry tetrahydrofuran (125 ml) under nitrogen at −78° C. is added dropwise a solution of methyl (3R)-3-(4-chlorophenyl)-3-cyclopropylpropanoate (6.5 g, 27.2 mmol) in dry tetrahydrofuran (50 ml). The reaction mixture is allowed to warm to 0° over 5 minutes, re-cooled to −78° C., and N-fluorobenzenesulfonimide (19.1 g, 60.6 mmol) is added.

The reaction is allowed to warm to room temperature, stirred an additional 2 hours, and then partitioned between ether (200 ml) and saturated ammonium chloride (200 ml). The solids are filtered off and the organic layer is separated, dried over anhydrous sodium sulfate, and concentrated in vacuo. The residue is chromatographed on silica gel eluting with ether:hexane (10:90) to yield the title compound as a colorless liquid (6.40 g, 92%) which is characterized by $^1$HNMR, IR and mass spectral analyses.

EXAMPLE 13

Preparation of Methyl (3S)-3-(4-chlorophenyl)-3-cyclopropyl-2-fluoropropanoate

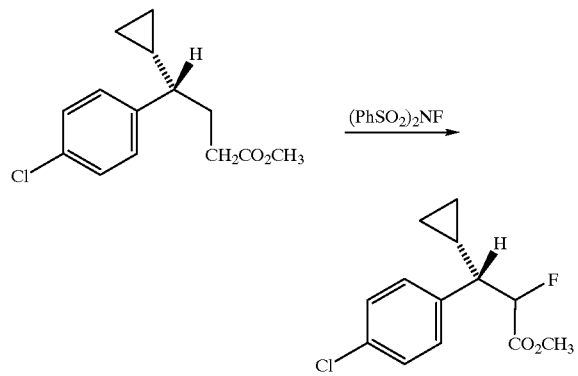

Using the procedure of Example 12, methyl (3S)-3-(4-chlorophenyl)-3-cyclopropylpropanoate yields the title compound as an off-white semi-solid which is characterized by $^1$HNMR, IR and mass spectral analyses.

EXAMPLE 14

Preparation of 4-Fluoro-3-phenoxybenzaldehyde

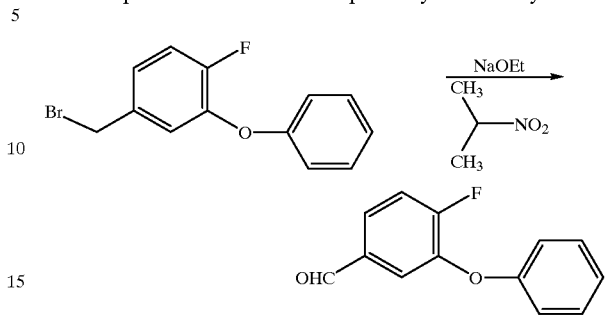

After dissolving sodium metal (0.41 g, 17.8 g-atom) in ethanol (25 ml), nitropropane (1.65 g) and 4-(bromomethyl)-1-fluoro-2-phenoxybenzene (5.00 g) are added and the mixture stirred for 3.5 h. The reaction was filtered and concentrated in vacuo. The residue is taken up in ether and washed with water (10 ml). The organic layer is dried over anhydrous sodium sulfate and concentrated in vacuo. The residue is chromatographed on silica gel eluting with ether:hexane (10:90) to afford the title compound as a colorless liquid which is characterized by $^1$HNMR spectral analyses.

EXAMPLE 15

Preparation of 1-Fluoro-4-[(E)-2-methoxyethenyl]-2-phenoxybenzene

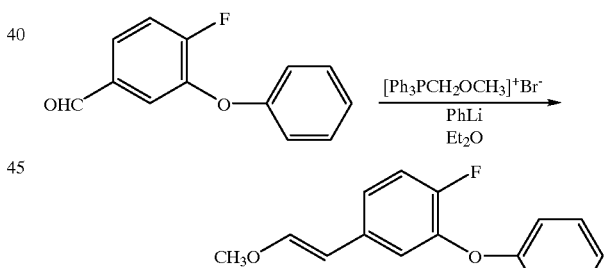

To a stirred suspension of (methoxymethyl)triphenylphosphonium chloride (2.48 g) in ether (50 ml) at room temperature under nitrogen is added phenyllithium (4 ml of a 1.8 M solution in ether, 7.2 mmol) and the resulting mixture stirred for 20 minutes. 4-fluoro-3-phenoxybenzaldehyde (1.30 g, 6.0 mmol) is then added and the reaction is stirred for 4 hours. The reaction mixture was diluted with saturated aqueous ammonium chloride (20 ml) and diethyl ether (50 ml). The organic layer is dried over anhydrous sodium sulfate and concentrated in vacuo. The residue is chromatographed on silica gel eluting with ether:hexane (5:95) to afford the title compound as a colorless liquid (1.30 g, 89%) which is characterized by $^1$HNMR, IR and mass spectral analyses.

EXAMPLE 16

Preparation of (4-Fluoro-3-2-phenoxyphenyl) acetaldehyde

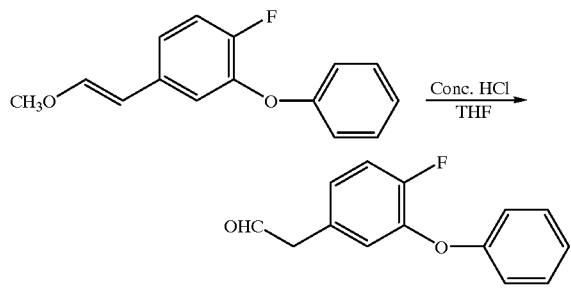

A mixture of 1-fluoro-4-[(E)-2-methoxyethenyl]-2-phenoxybenzene (0.50 g), concentrated hydrochloric acid (2 ml) and tetrahydrofuran (10 ml) is stirred at room temperature for 1 hour. The reaction is diluted with water (100 ml), the organic layer is separated and dried over anhydrous sodium sulfate, and the solvent is removed in vacuo to give the title compound as a colorless liquid (0.43 g, 41%) which is characterized by $^1$HNMR, mass spectral analyses and used without further purification.

EXAMPLE 17

Preparation of Methyl 2-[(4-chlorophenyl) (cyclopropyl)methyl-2-fluoro-4-(4-fluoro-3-phenoxyphenyl)-3-hydroxybutanoate [(SRR and (SRS or SSR)] and Methyl 2-[(4-chlorophenyl) (cyclopropyl)methyl-2-fluoro-4-(4-fluoro-3-phenoxyphenyl)-3-hydroxybutanoate [(SSS) and (SSR or SRS)]

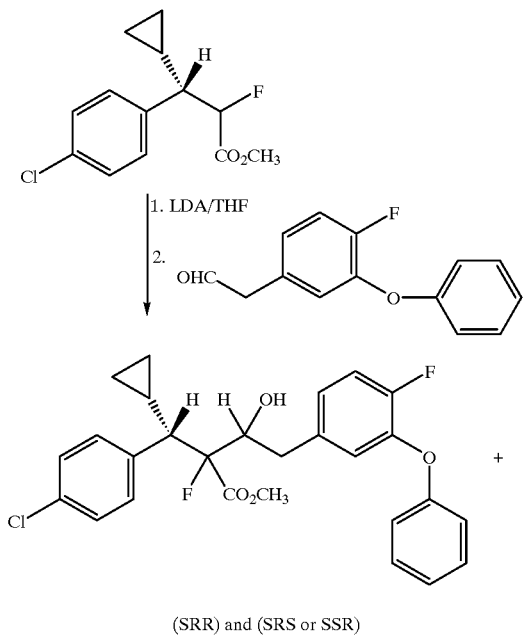

(SRR) and (SRS or SSR)

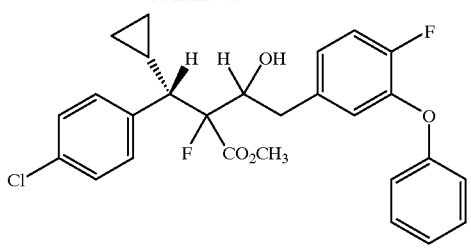

(SSS) and (SSR or SRS)

To a stirred solution of a lithium diisopropylamide in tetrahydrofuran (7.75 ml of 2M lithium diisopropylamide in tetrahydrofuran added to 50 ml of dry tetrahydrofuran) under nitrogen at −78° C. is added dropwise a solution of methyl (3S)-3-(4-chlorophenyl)-3-cyclopropyl-2-fluoropropanoate (3.6 g, 11.9 mmol) in dry tetrahydrofuran, and the resulting mixture stirred for 15 minutes. A solution of (4-fluoro-3-phenoxyphenyl)acetaldehyde (3.23 g, 14.0 mmol) in dry tetrahydrofuran is then added dropwise and the resulting mixture is stirred for 2 hours at −78° C. The reaction is quenched at −78° C. with saturated aqueous ammonium chloride (2 ml) and partitioned between ether (50 ml) and water (50 ml). The organic layer is separated, dried over anhydrous sodium sulfate and concentrated in vacuo. The residue is chromatographed on silica gel eluting with ether:hexane (25:75) to yield methyl 2-[(4-chlorophenyl)(cyclopropyl)methyl-2-fluoro-4-(4-fluoro-3-phenoxyphenyl)-3-hydroxybutanoate [(SRR) and (SRS or SSR)] (1.17 g) as a colorless oil, and Methyl 2-[(4-chlorophenyl)(cyclopropyl)methyl-2-fluoro-4-(4-fluoro-3-phenoxyphenyl)-3-hydroxybutanoate [(SSS) and (SSR or SRS)] (1.65 g) as a colorless oil, both of which are characterized by $^1$HNMR and $^{19}$FNMR spectral analyses. The overall yield based on recovered starting materials is 50%.

EXAMPLE 18

Preparation of Methyl 2-[(4-chlorophenyl) (cyclopropyl)methyl-2-fluoro-4-(4-fluoro-3-phenoxyphenyl)-3-hydroxybutanoate [(RSS) and (RSR) or (RRS)] and Methyl 2-[(4-chlorophenyl) (cyclopropyl)methyl-2-fluoro-4-(4-fluoro-3-phenoxyphenyl)-3-hydroxybutanoate [(RRR) and (RSR or RRS)]

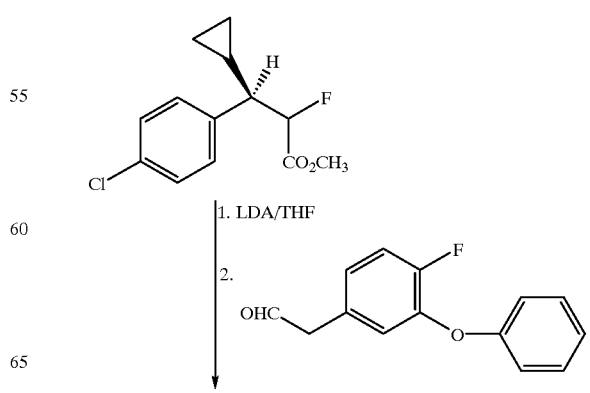

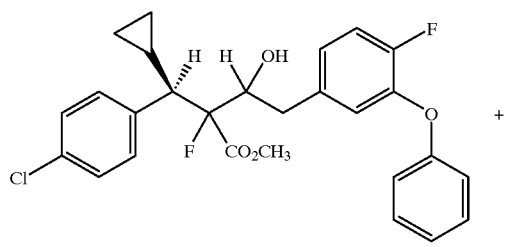

(RSS) and (RSR or RRS)

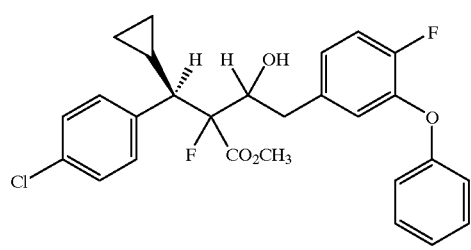

(RRR) and (RSR or RRS)

Using the procedure of Example 17, methyl (3R)-3-(4-chlorophenyl)-3-cyclopropyl-2-fluoropropanoate yields the title compounds which are characterized by $^1$HNMR and $^{19}$FNMR spectral analyses.

EXAMPLE 19

Preparation of Methyl (2R,3R)-3-(acetyloxy)2-[(S)-(4-chlorophenyl)(cyclopropyl)methyl]-2-fluoro-4-(4-fluoro-3-phenoxyphenyl)butanoate (SRR isomer) and methyl (2R,3S or 2S,3R)-3-(acetyloxy)2-[(S)-(4-chlorophenyl)(cyclopropyl)methyl]-2-fluoro-4-(4-fluoro-3-phenoxyphenyl)butanoate (SRS or SSR isomer/Diastereomer A)

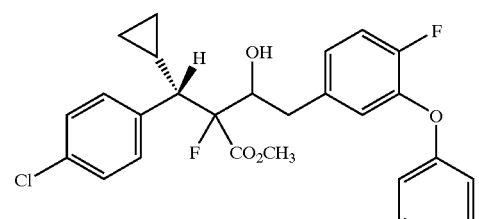

(SRR) and (SRS or SSR)

Ac₂O
DMAP
CH₂Cl₂

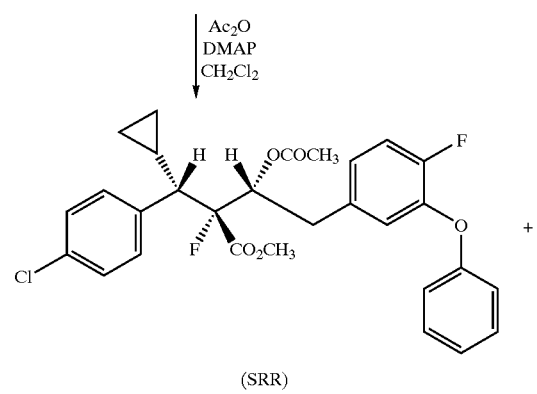

(SRR)

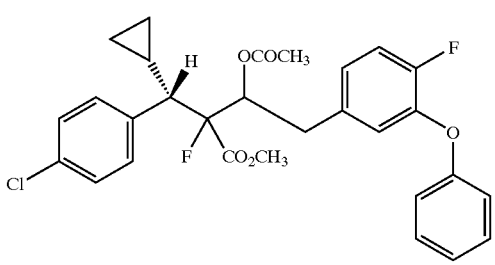

Diastereomer A
(SSR or SRS)

A solution of methyl 2-[(4-chlorophenyl)(cyclopropyl)methyl-2-fluoro-4-(4-fluoro-3-phenoxyphenyl)-3-hydroxybutanoate [(SRR) and (SRS or SSR)] (1.17 g, 2.40 mmol), acetic anhydride (1.50 ml) and dimethylaminopyridine (0.11 g) in methylene chloride is stirred for 2 hours at room temperature (30 ml). The solvent is removed in vacuo and the residue is chromatographed on silica gel eluting with ether:hexane (15:85) to afford methyl (2S,3S)-3-(acetyloxy)-2-[(S)-(4-chlorophenyl)(cyclopropyl)methyl]-2-fluoro-4-(4-fluoro-3-phenoxyphenyl)butanoate (0.20 g) and methyl (2R,3S or 2S,3R)-3-(acetyloxy)2-[(S)-(4-chlorophenyl)(cyclopropyl)methyl]-2-fluoro-4-(4-fluoro-3-phenoxyphenyl)butanoate (SRS or SSR isomer/Diastereomer A) (0.80 g) as pure diastereomers in 79% overall yield and >98% ee as determined by $^{19}$FNMR spectral analysis.

EXAMPLE 20

Preparation of Methyl (2S,3S)-3-(acetyloxy)-2-[(S)-(4-chlorophenyl)(cyclopropyl)methyl]-2-fluoro-4-(4-fluoro-3-phenoxyphenyl)butanoate (SSS isomer) and methyl ((2R,3S or 2S,3R)-3-(acetyloxy)-2-[(S)-(4-chlorophenyl)(cyclopropyl)methyl]-2-fluoro-4-(4-fluoro-3-phenoxyphenyl)butanoate (SRS or SSR isomer/Diastereomer B)

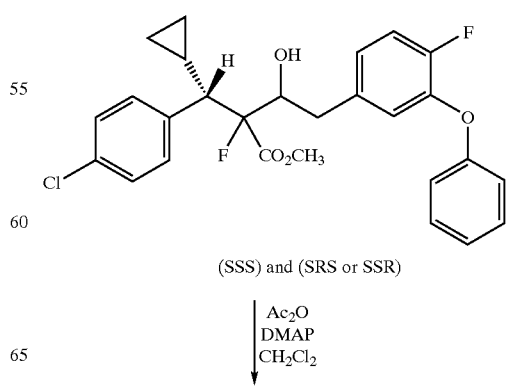

(SSS) and (SRS or SSR)

Ac₂O
DMAP
CH₂Cl₂

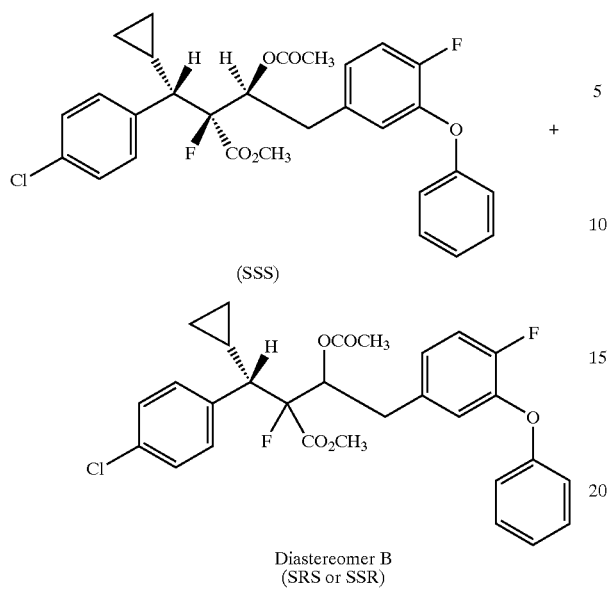

(SSS)

Diastereomer B
(SRS or SSR)

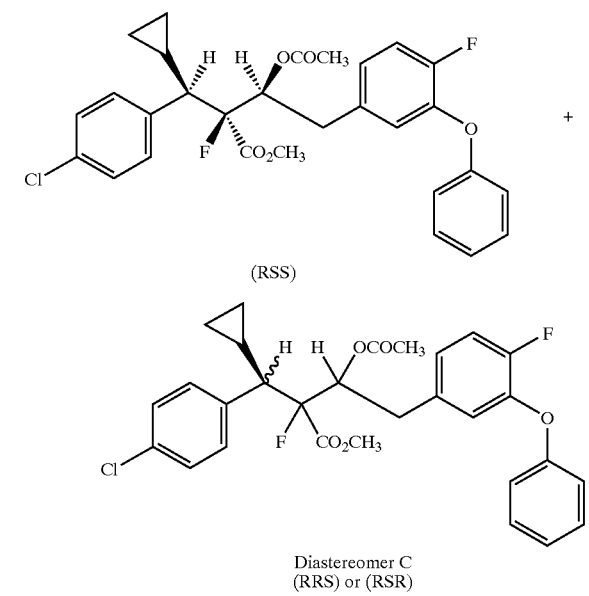

(RSS)

Diastereomer C
(RRS) or (RSR)

Using the procedure of Example 19, methyl 2-[(4-chlorophenyl)(cyclopropyl)methyl-2-fluoro-4-(4-fluoro-3-phenoxyphenyl)-3-hydroxybutanoate {(SSS) and (SRS or SSR)] affords the title compounds as pure diastereomers which are characterized by $^1$HNMR and $^{19}$FNMR spectral analyses.

Using the procedure of Example 19, methyl 2-[(4-chlorophenyl)(cyclopropyl)methyl-2-fluoro-4-(4-fluoro-3-phenoxyphenyl)-3-hydroxybutanoate [(RSS) and (RSR or RRS)] yields the title compounds as pure diastereomers which are characterized by $^1$HNMR and $^{19}$FNMR spectral analyses.

EXAMPLE 21

Preparation of Methyl (2S,3S)-3-(acetyloxy)-2-[(R)-(4-chlorophenyl)(cyclopropyl)methyl]-2-fluoro-4-(4-fluoro-2-phenoxyphenyl)butanoate (RSS isomer) and Methyl (2S,3R or 2R,3S)-3-(acetyloxy)-2-[(R)-(4-chlorophenyl)(cyclopropyl)methyl]-2-fluoro-4-(4-fluoro-2-phenoxyphenyl)butanoate (RSR or RRS/Diastereomer C)

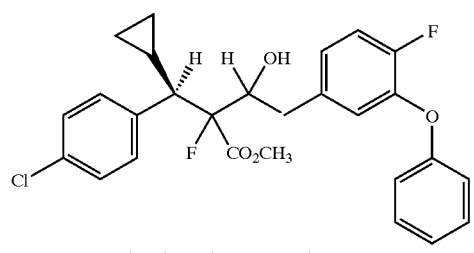

(RSS) and (RSR or RRS)

| Ac$_2$O
| DMAP
| CH$_2$Cl$_2$
↓

EXAMPLE 22

Preparation of Methyl (2R,3R)-3-(acetyloxy)-2-[(R)-(4-chlorophenyl)(cyclopropyl)methyl]-2-fluoro-4-(4-fluoro-3-phenoxyphenyl)butanoate (R,R,R) and Methyl (2S,3R or 2R,3S)-3-(acetyloxy)-2-[(R)-(4-chlorophenyl)(cyclopropyl)methyl]-2-fluoro-4-(4-fluoro-3-phenoxyphenyl)butanoate (RSR or RRS/Diastereomer D)

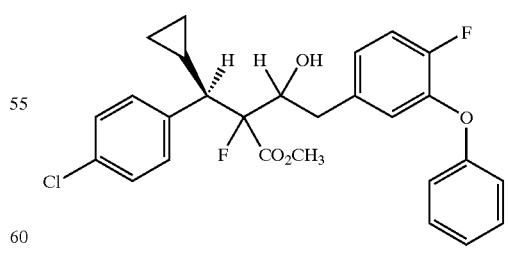

(RRR) and (RSR or RRS)

| Ac$_2$O
| DMAP
| CH$_2$Cl$_2$
↓

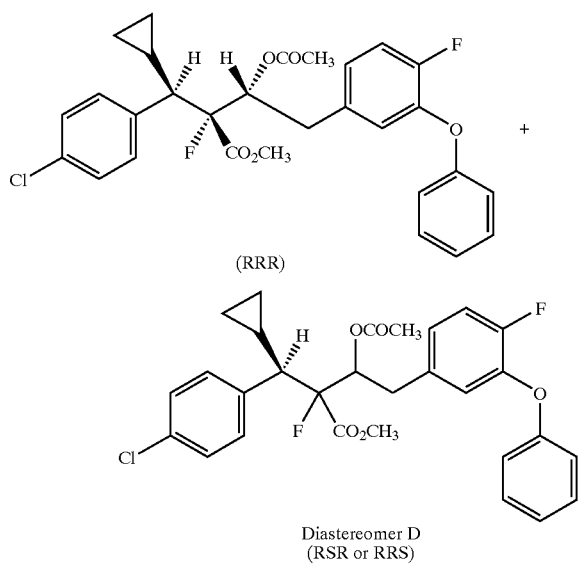

(RRR)

Diastereomer D
(RSR or RRS)

Using the procedure of Example 19, methyl 2-[(4-chlorophenyl)(cyclopropyl)methyl-2-fluoro-4-(4-fluoro-3-phenoxyphenyl)-3-hydroxybutanoate [(RRR) and (RSR or RRS)] yields the title compounds as pure diastereomers which are characterized by $^1$HNMR and $^{19}$FNMR spectral analysis. The structure of methyl (2S,3S)-3-(acetyloxy)-2-[(R)-(4-chlorophenyl)(cyclopropyl)methyl]-2-fluoro-4-(4-fluoro-3-phenoxyphenyl)butanoate is also confirmed by x-ray crystal structure analysis.

EXAMPLE 23

Preparation of (2R,3S or 2S,3R)-2-[(S)-(4-chlorophenyl(cyclopropyl)methyl]-2-fluoro-4-(4-fluoro-3-phenoxyphenyl)-3-hydroxybutanoic acid (SRS or SRR/Diastereomer E)

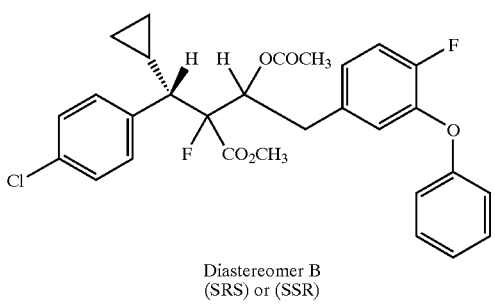

Diastereomer B
(SRS) or (SSR)

↓ 10% aq. NaOH
CH$_3$OH
THF

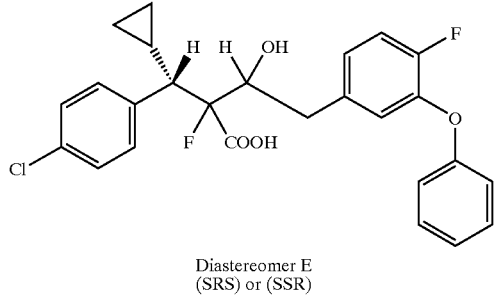

Diastereomer E
(SRS) or (SSR)

A mixture of methyl (2R,3S or 2S,3R)-3-(acetyloxy)-2-[(S)-(4-chlorophenyl)(cyclopropyl)methyl]-2-fluoro-4-(4-fluoro-3-phenoxyphenyl)butanoate (Diastereomer B) (0.80 g, 1.50 mmol), aqueous sodium hydroxide (25 ml), methanol (20 ml) and tetrahydrofuran (5 ml) is refluxed for 1 hour. The organic solvents are removed in vacuo, the mixture is diluted with ethyl acetate and acidified to pH 3 with concentrated hydrochloric acid. The organic layer is separated, dried over anhydrous sodium sulfate and concentrated in vacuo to afford the title compound as a colorless semi solid, which is characterized by $^1$HNMR and $^{19}$FNMR and used without further purification.

EXAMPLE 24

Preparation of (2S,3R or 2R,3S)-2-[(S)-(4-chlorophenyl(cyclopropyl)methyl]-2-fluoro-4-(4-fluoro-3-phenoxyphenyl)-3-hydroxybutanoic acid (Diastereomer F)

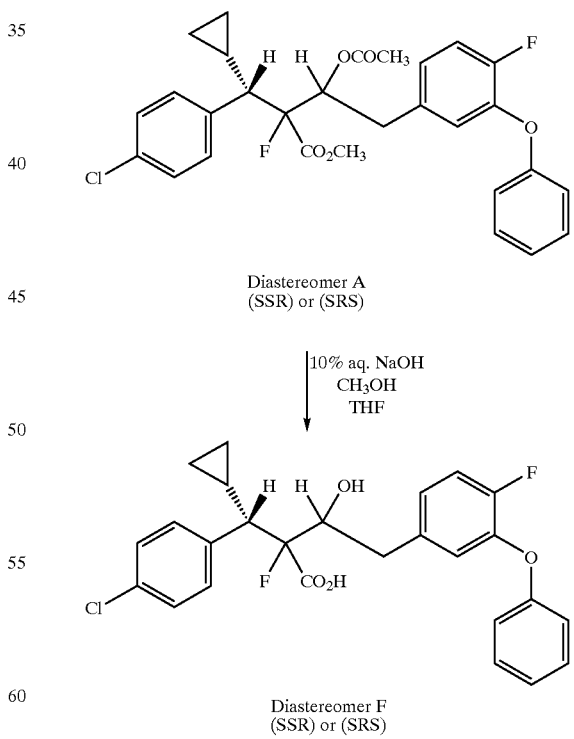

Diastereomer A
(SSR) or (SRS)

↓ 10% aq. NaOH
CH$_3$OH
THF

Diastereomer F
(SSR) or (SRS)

Using the procedure of Example 23, methyl (2S,3R or 2R,3S)-3-(acetyloxy)-2-[(S)-(4-chlorophenyl)(cyclopropyl)methyl]-2-fluoro-4-(4-fluoro-3-phenoxyphenyl)butanoate (Diastereomer A) yields the title compound as a pure dias-

EXAMPLE 25

Preparation of (2S,3S)-2-[(S)-(4-chlorophenyl)(cyclopropyl)methyl]-2-fluoro-4-(4-fluoro-3-phenoxyphenyl)-3-hydroxybutanoic acid

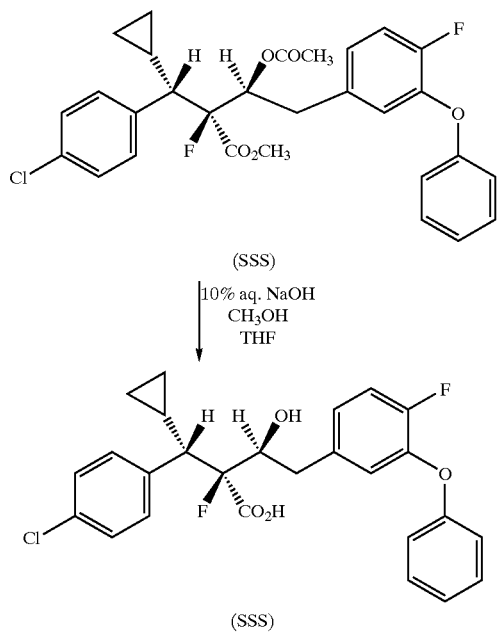

(SSS)

↓ 10% aq. NaOH
  CH₃OH
  THF (SSS)

Using the procedure of Example 23, methyl (2S,3S)-3-(acetyloxy)-2-[(S)-(4-chlorophenyl)(cyclopropyl)methyl]-2-fluoro-4-(4-fluoro-3-phenoxyphenyl)butanoate yields (2S,3S)-2-[(S)-(4-chlorophenyl)(cyclopropyl)methyl]-2-fluoro-4-(4-fluoro-3-phenoxyphenyl)-3-hydroxybutanoic acid as a pure diastereomer which is characterized by $^1$HNMR and $^{19}$FNMR spectral analyses.

EXAMPLE 26

Preparation of (2R,3R)-2-[(S)-(4-chlorophenyl)(cyclopropyl)methyl]-2-fluoro-4-(4-fluoro-3-phenoxyphenyl)-3-hydroxybutanoic acid

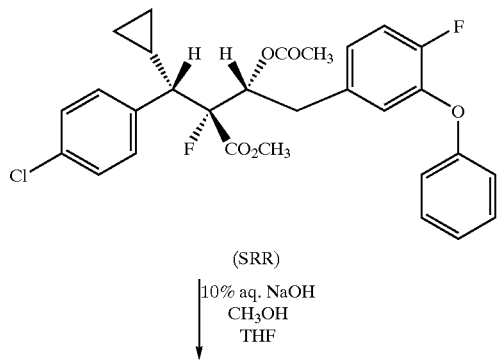

(SRR)

↓ 10% aq. NaOH
  CH₃OH
  THF

-continued

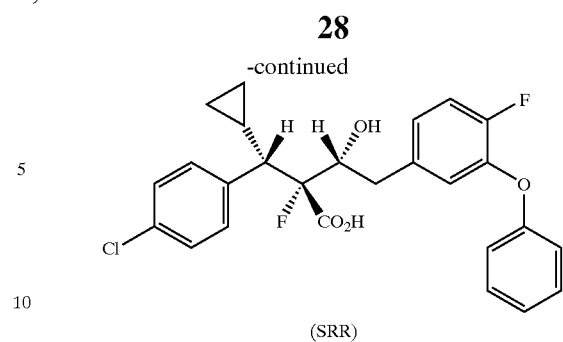

(SRR)

Using the procedure of Example 23, methyl (2R,3R)-3-(acetyloxy)2-[(S)-(4-chlorophenyl)(cyclopropyl)methyl]-2-fluoro-4-(4-fluoro-3-phenoxyphenyl)butanoate yields the title compound as a pure diastereomer which is characterized by $^1$HNMR and $^{19}$FNMR spectral analyses.

EXAMPLE 27

Preparation of (2R,3R)-2-[(R)-(4-chlorophenyl)(cyclopropyl)methyl]-2-fluoro-4-(4-fluoro-3-phenoxyphenyl)-3-hydroxybutanoic acid

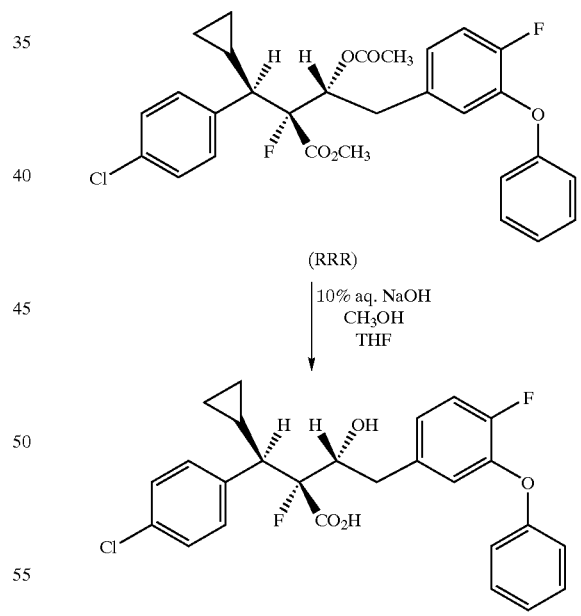

(RRR)

↓ 10% aq. NaOH
  CH₃OH
  THF (RRR)

Using the procedure of Example 23, methyl (2R,3R)-3-(acetyloxy)-2-[(R)-(4-chlorophenyl)(cyclopropyl)methyl]-2-fluoro-4-(4-fluoro-3-phenoxyphenyl)butanoate yields the title compound as a pure diastereomer which is characterized by $^1$HNMR and $^{19}$FNMR spectral analyses.

EXAMPLE 28

Preparation of (2S,3R or 2R,3S)-2-[(R)-(4-chlorophenyl)(cyclopropyl)methyl]-2-fluoro-4-(4-fluoro-3-phenoxyphenyl)-3-hydroxybutanoic acid

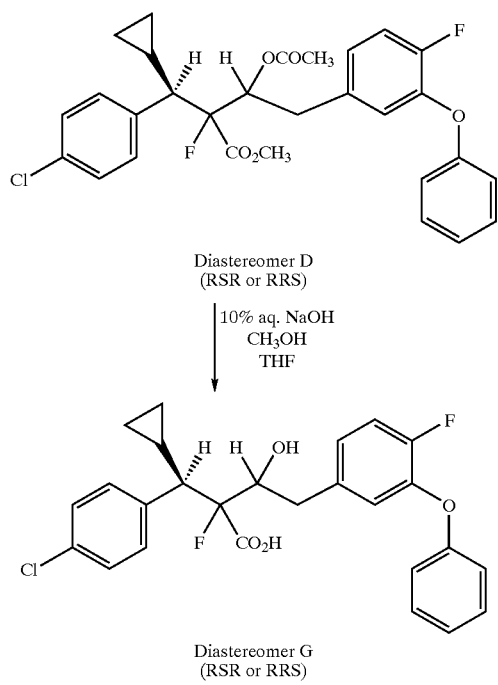

Diastereomer D
(RSR or RRS)

10% aq. NaOH
CH₃OH
THF

Diastereomer G
(RSR or RRS)

Using the procedure of Example 23, methyl (2S,3R or 2R,3S)-3-(acetyloxy)-2-[(R)-(4-chlorophenyl)(cyclopropyl)methyl]-2-fluoro-4-(4-fluoro-3-phenoxyphenyl)butanoate (Diastereomer D) yields the title compound as a pure diastereomer which is characterized by $^{1}$HNMR and $^{19}$FNMR spectral analyses.

EXAMPLE 29

Preparation of 4-[(2Z,4S)-4-(4-chlorophenyl)-4-cyclopropyl-3-fluoro-2-butenyl]-1-fluoro-2-phenoxybenzene

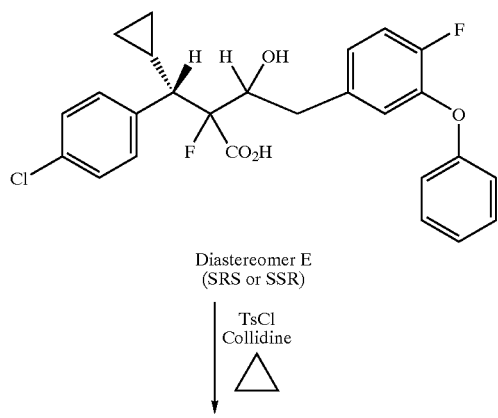

Diastereomer E
(SRS or SSR)

TsCl
Collidine

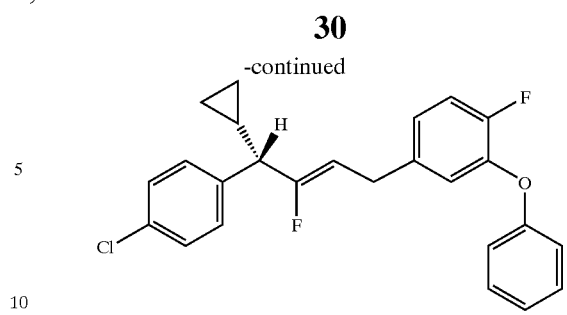

A solution of crude (2R,3S or 2S,3R)-2-[(S)-(4-chlorophenyl)(cyclopropyl)methyl]-2-fluoro-4-(4-fluoro-3-phenoxyphenyl)-3-hydroxybutanoic acid (Diastereomer E) (0.72 g, 1.5 mmol), tosyl chloride (0.58 g, 3.0 mmol) and collidine (20 ml) is heated at 170° C. for 2 hours. The mixture is concentrated in vacuo and the residue chromatographed on silica gel eluting with ether:hexane (5:95) to yield the title compound as a colorless liquid (0.43 g, 69% from diasteriomer B), [α]$_D$=+35.8 (C=0.0438, CHCl₃) which is characterized by $^{1}$HNMR and $^{19}$FNMR spectral analyses.

EXAMPLE 30

Preparation of 4-[(2Z,4S)-4-(4-Chlorophenyl)-4-cyclopropyl-3-fluoro-2-butenyl]-1-fluoro-2-phenoxybenzene

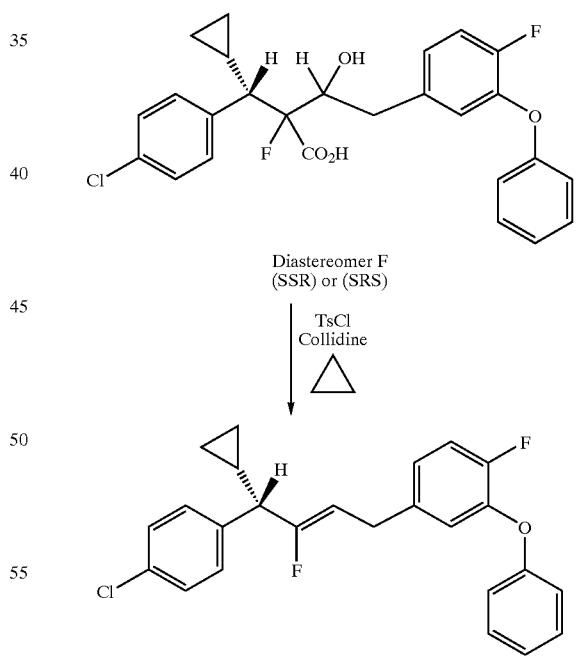

Using the procedure of Example 29, (2S,3R or 2R,3S)-2-[(S)-(4-chlorophenyl)(cyclopropyl)methyl]-2-fluoro-4-(4-fluoro-3-phenoxyphenyl)-3-hydroxybutanoic acid (Diastereomer F) yields the title compound as a colorless fluid which is characterized by $^{1}$HNMR and $^{19}$FNMR spectral analyses.

EXAMPLE 31

Preparation of 4-[(2E,4S)-4-(4-chlorophenyl)-4-cyclopropyl-3-fluoro-2-butenyl]-1-fluoro-2-phenoxybenzene

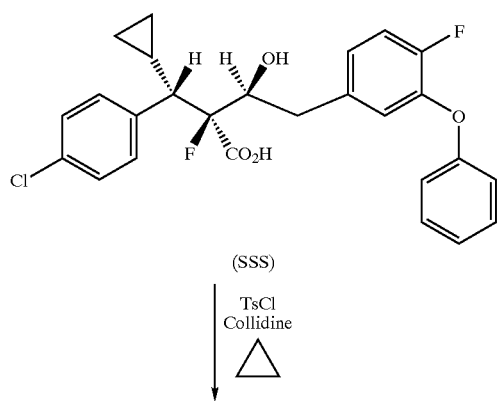

(SSS)

TsCl
Collidine
Δ

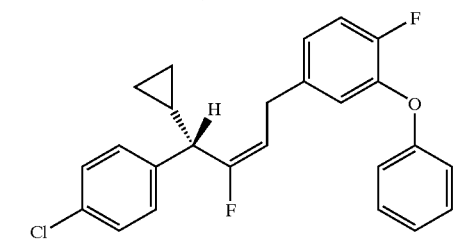

Using the procedure of Example 29, (2S,3S)-2-[(S)-(4-chlorophenyl)(cyclopropyl)methyl]-2-fluoro-4-(4-fluoro-3-phenoxyphenyl)-3-hydroxybutanoic acid yields the title compound as a colorless liquid which is characterized by $^1$HNMR and $^{19}$FNMR spectral analyses.

EXAMPLE 32

Preparation of 4-[(2E,4S)-4-(4-chlorophenyl)-4-cyclopropyl-3-fluoro-2-butenyl]-1-fluoro-2-phenoxybenzene

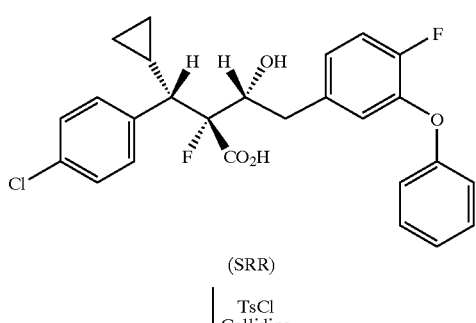

(SRR)

TsCl
Collidine
Δ

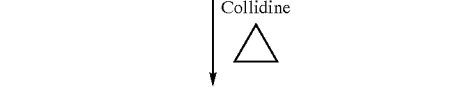

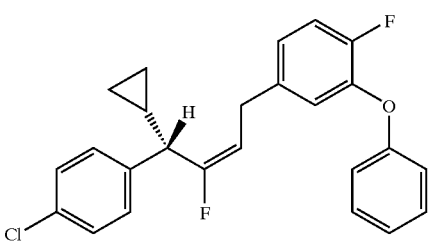

Using the procedure of Example 29, (2R,3R)-2-[(S)-(4-chlorophenyl)(cyclopropyl)methyl]-2-fluoro-4-(4-fluoro-3-phenoxyphenyl)-3-hydroxybutanoic acid yields the title compound as a colorless liquid which is characterized by $^1$HNMR and $^{19}$FNMR spectral analyses.

EXAMPLE 33

Preparation of 4-[(2E,4R)-4-(4-Chlorophenyl)-4-cyclopropyl-3-fluoro-2-butenyl]-1-fluoro-2-phenoxybenzene

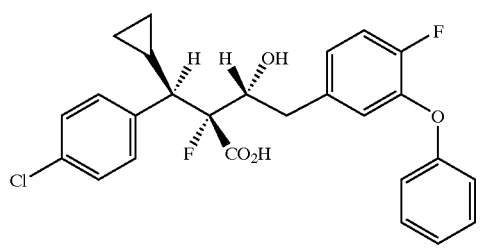

(RRR)

TsCl
Collidine
Δ

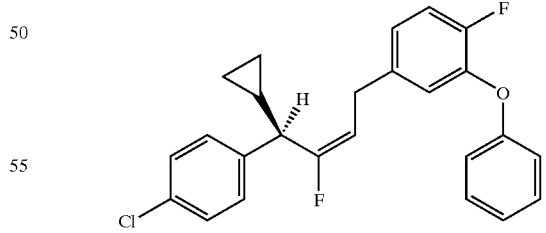

Using the procedure of Example 29, (2R,3R)-2-[(R)-(4-chlorophenyl)(cyclopropyl)methyl]-2-fluoro-4-(4-fluoro-3-phenoxyphenyl)-3-hydroxybutanoic acid yields the title compound as a colorless liquid which is characterized by $^1$HNMR and $^{19}$FNMR spectral analyses.

EXAMPLE 34

Preparation of 4-[(2Z,4R)-4-(4-chlorophenyl)-4-cyclopropyl-3-fluoro-2-butenyl]-1-fluoro-2-phenoxybenzene

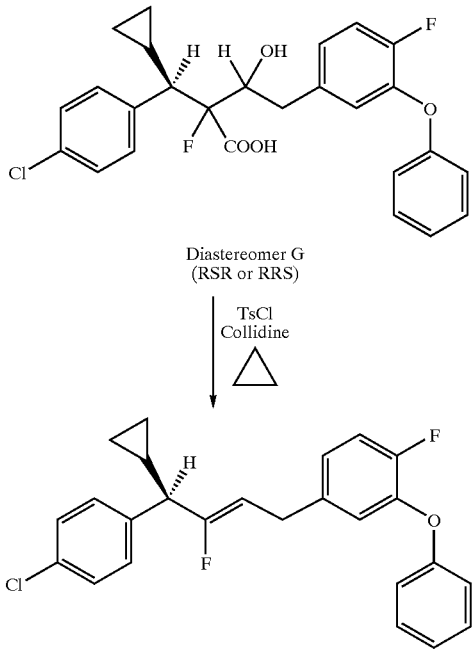

Diastereomer G
(RSR or RRS)

TsCl
Collidine

Using the procedure of Example 29, (2S,3R or 2R,3S)-2-[(R)-(4-chlorophenyl)(cyclopropyl)methyl]-2-fluoro-4-(fluoro-3-phenoxyphenyl)-3-hydroxybutanoic acid (Diastereomer G) yields 4-[(2Z,4R)-4-(4-chlorophenyl)-4-cyclopropyl-3-fluoro-2-butenyl]-1-fluoro-2-phenoxybenzene as a colorless oil which is charactorized by $^1$HNMR and $^{19}$FNMR spectral analysis.

What is claimed is:

1. A process for the preparation of a chiral compound of formula I

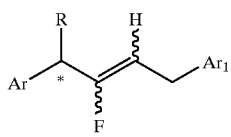

wherein
  Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups,
    1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
    a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
  R is $C_1$–$C_4$alkyl, $C_1$–$C_4$haloalkyl, $C_3$–$C_6$cycloalkyl or $C_3$–$C_6$halocycloalkyl;
  $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
    phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
    a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
  the (E)- and (Z)- isomers thereof,
which process comprises the following steps:
  a) treating a racemic ester of formula II

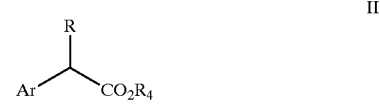

wherein Ar and R are defined as hereinabove and $R_4$ is $C_1$–$C_4$alkyl with an esterase to form a first mixture of either R-acid IIIa and S-ester IIIb

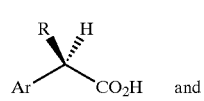

and

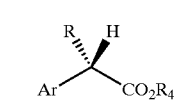

or of S-acid IIIc and R-ester IIId

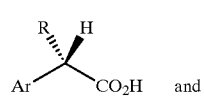

and

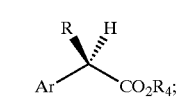

b) separating said acid IIIa or IIIc from said ester IIIb or IIId;

c) reducing said acid IIIa or IIIc or said ester IIIb or IIId to obtain a chiral alcohol IV having the R- or S-configuration

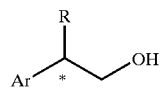

IV d) reacting said chiral alcohol with an arylsulfonyl halide $Ar_2SO_2X$ wherein $Ar_2$ is phenyl, p-chlorophenyl, or p-tolyl, and X is chloro, bromo or fluoro to afford a sulfonate of formula V

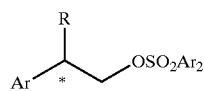

V e) reacting said sulfonate V with a cyanide-delivering agent to afford a nitrile of formula VI

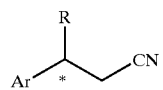

VI f) hydrolyzing said nitrile VI to afford an acid of formula VII

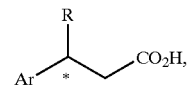

VII g) esterifying said acid VII with an alcohol $R_1OH$, wherein $R_1$ is $C_1$–$C_4$alkyl to afford an ester of formula VIII

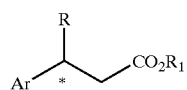

VIII h) fluorinating said ester to afford a fluoro-ester of formula IX

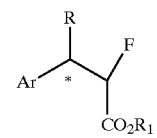

IX i) reacting said fluoro ester with an aldehyde $Ar_1CH_2CHO$, wherein $Ar_1$ is defined as hereinabove, in a solvent in the presence of a base to afford a second mixture of 4 chiral diastereomeric hydroxy-esters of formula X;

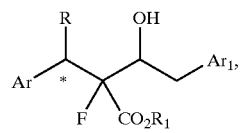

X j) optionally separating said second mixture X into a third mixture Xa and a forth mixture Xb, each mixture having two chiral diastereomers;

k) treating said hydroxy-ester mixture X, Xa or Xb with an acylating agent $R_2COX_1$, wherein $R_2$ is $C_1$–$C_4$alkyl and $X_1$ is Cl, Br or $R_2COO$, to afford a fifth mixture of 4 chiral diastereomeric acyloxy esters XI, a sixth mixture of 2 acyloxy esters of formula XIa, or a seventh mixture of 2 chiral diastereomeric acyloxy esters XIb

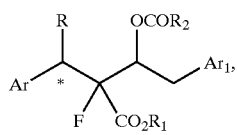

XI l) optionally separating said sixth or seventh mixture into essentially pure chiral diastereomeric acyloxy esters;

m) hydrolyzing said pure chiral acyloxy esters or mixtures of esters of formula XI to afford a hydroxy-acid of formula XII,

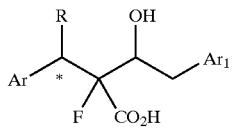

XII and n) heating said hydroxy-acid XII with an arylsulfonyl halide $Ar_3SO_2X_2$, wherein $Ar_3$ is phenyl, p-chlorophenyl, or p-tolyl, and $X_2$ is chloro or bromo to afford the desired chiral compound of formula I.

2. The process according to claim 1 wherein said esterase is horse liver esterase.

3. The process according to claim 1 wherein said base is lithium diisopropylamide.

4. The process according to claim 1 wherein said solvent is tetrahydrofuran.

5. The process according to claim 1 wherein $R_4$ is methyl.

6. A chiral compound of the following formula

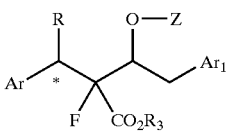

XIII wherein

Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy or hydroxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is $C_1$–$C_4$alkyl, $C_1$–$C_4$haloalkyl, $C_3$–$C_6$cycloalkyl or $C_3$–$C_6$halocycloalkyl;

$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and $R_3$ is H or $C_1$–$C_4$ alkyl; and Z is H or $COR_2$, wherein $R_2$ is $C_1$–$C_4$alkyl.

7. The compound according to claim 6 wherein

Ar is phenyl optionally substituted with any combination of from one to three halogen, $C_1$–$C_4$alkyl, $C_2$–$C_4$haloalkyl, $C_1$–$C_4$alkoxy or $C_1$–$C_4$haloalkoxy groups; and R is $C_1$–$C_4$alkyl or $C_3$–$C_6$cycloalkyl.

8. The compound according to claim 7 wherein $Ar_1$ is phenyl optionally substituted with one to three halogen groups; and R is $C_3$–$C_6$cycloalkyl.

9. The compound according to claim 8 selected from the group consisting of methyl (2S,3S)-2[(R)-(4-chlorophenyl)(cyclopropyl)methyl]-2-fluoro-4-(4-fluoro-3-phenoxyphenyl)butanoate;

methyl (2R,3R)-2-[(R)-(4-chlorophenyl)(cyclopropyl)methyl]-2-fluoro-4-(4-fluoro-3-phenoxyphenyl)butanoate;

methyl (2S,3R)-2-[(R)-(4-chlorophenyl)(cyclopropyl)methyl]-2-fluoro-4-(4-fluoro-3-phenoxyphenyl)butanoate;

methyl (2R,3S)-2-[(R)-(4-chlorophenyl)(cyclopropyl)methyl]-2-fluoro-4-(4-fluoro-3-phenoxyphenyl)butanoate;

methyl (2S,3S)-2-[(S)-(4-chlorophenyl)(cyclopropyl)methyl]-2-fluoro-4-(4-fluoro-3-phenoxyphenyl)butanoate;

methyl (2R,3R)-2-[(S)-(4-chlorophenyl)(cyclopropyl)methyl]-2-fluoro-4-(4-fluoro-3-phenoxyphenyl)butanoate;

methyl (2S,3R)-2-[(S)-(4-chlorophenyl)(cyclopropyl)methyl]-2-fluoro-4-(4-fluoro-3-phenoxyphenyl)butanoate;

methyl (2R,3S)-2-[(S)-(4-chlorophenyl)(cyclopropyl)methyl]-2-fluoro-4-(4-fluoro-3-phenoxyphenyl)butanoate;

methyl (2S,3S)-3-(acetyloxy)-2-[(S)-(4-chlorophenyl)(cyclopropyl)methyl]-2-fluoro-4-(4-fluoro-3-phenoxyphenyl)butanoate;

methyl (2R,3R)-3-(acetyloxy)-2-[(S)-(4-chlorophenyl)(cyclopropyl)methyl]-2-fluoro-4-(4-fluoro-3-phenoxyphenyl)butanoate;

methyl (2R,3R)-3-(acetyloxy)-2-[(S)-(4-chlorophenyl)(cyclopropyl)methyl]-2-fluoro-4-(4-fluoro-3-phenoxyphenyl)butanoate;

methyl (2S,3R)-3-(acetyloxy)-2-[(S)-(4-chlorophenyl)(cyclopropyl)methyl]-2-fluoro-4-(4-fluoro-3-phenoxyphenyl)butanoate;

methyl (2S,3S)-3-(acetyloxy)-2-[(R)-(4-chlorophenyl)(cyclopropyl)methyl]-2-fluoro-4-(4-fluoro-3-phenoxyphenyl)butanoate;

methyl (2R,3R)-3-(acetyloxy)-2-[(R)-(4-chlorophenyl)(cyclopropyl)methyl]-2-fluoro-4-(4-fluoro-3-phenoxyphenyl)butanoate;

methyl (2R,3S)-3-(acetyloxy)-2-[(R)-(4-chlorophenyl)(cyclopropyl)methyl]-2-fluoro-4-(4-fluoro-3-phenoxyphenyl)butanoate;

methyl (2S,3R)-3-(acetyloxy)-2-[(R)-(4-chlorophenyl)-(cyclopropyl)methyl]-2-fluoro-4-(4-fluoro-3-phenoxyphenyl)butanoate;

(2S,3S)-2-[(S)-(4-chlorophenyl)(cyclopropyl)methyl]-2-fluoro-4-(4-fluoro-3-phenoxyphenyl)-3-hydroxybutanoic acid;

(2R,3R)-2-[(S)-(4-chlorophenyl)(cyclopropyl)methyl]-2-fluoro-4-(4-fluoro-3-phenoxyphenyl)-3-hydroxybutanoic acid;

(2R,3S)-2-[(S)-(4-chlorophenyl)(cyclopropyl)methyl]-2-fluoro-4-(4-fluoro-3-phenoxyphenyl)-3-hydroxybutanoic acid;

(2S,3R)-2-[(S)-(4-chlorophenyl)(cyclopropyl)methyl]-2-fluoro-9-(4-fluoro-3-phenoxyphenyl)-3-hydroxybutanoic acid;

(2S,3S)-2-[(R)-(4-chlorophenyl)(cyclopropyl)methyl]-2-fluoro-4-(4-fluoro-3-phenoxyphenyl)-3-hydroxybutanoic acid;

(2R,3R)-2-[(R)-(4-chlorophenyl)(cyclopropyl)methyl]-2-fluoro-4-(4-fluoro-3-phenoxyphenyl)-3-hydroxybutanoic acid;

(2R,3S)-2-[(R)-(4-chlorophenyl)(cyclopropyl)methyl]-2-fluoro-4-(4-fluoro-3-phenoxyphenyl)-3-hydroxybutanoic acid; and (2S,3R)-2-[(R)-(4-chlorophenyl)(cyclopropyl)methyl]-2-fluoro-4-(4-fluoro-3-phenoxyphenyl)-3-hydroxybutanoic acid.

10. A chiral compound of the following formula

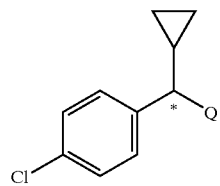

wherein

Q is —CH$_2$OH; —CH$_2$OSO$_2$Ar$_2$; —CH$_2$CN; —CH$_2$CO$_2$H; —CH$_2$CO$_2$R$_1$; or —CHFCO$_2$R$_1$;

Ar$_2$ is phenyl, p-chlorophenyl or p-tolyl; and

R$_1$ is C$_1$–C$_4$ alkyl.

11. The compound according to claim 10 selected from the group consisting of (2R)-2-(4-chlorophenyl)-2-cyclopropylethyl 4-methylbenzenesulfonate;

(2S)-2-(4-chlorophenyl)-2-cyclopropylethyl 4-methylbenzenesulfonate;

(3R)-3-(4-chlorophenyl)-3-cyclopropylpropanenitrile;

(3S)-3-(4-chlorophenyl)-3-cyclopropylpropanenitrile;

(3R)-3-(4-chlorophenyl)-3-cyclopropylpropanoic acid;

(3S)-3-(4-chlorophenyl)-3-cyclopropylpropanoic acid;

methyl (3R)-3-(4-chlorophenyl)-3-cyclopropylpropanoate;

methyl (3S)-3-(4-chlorophenyl)-3-cyclopropylpropanoate;

methyl (3R)-3-(4-chlorophenyl)-3-cyclopropyl-2-fluoropropanoate; and methyl (3S)-3-(4-chlorophenyl)-3-cyclopropyl-2-fluoropropanoate.

* * * * *